United States Patent [19]

Joet

[11] Patent Number: 4,665,734
[45] Date of Patent: May 19, 1987

[54] METHOD AND INSTALLATION FOR SELECTIVE DETECTION OF DEFECTS IN A WORKPIECE

[75] Inventor: Francois Joet, Genay, France
[73] Assignee: S.A. Vallourec, Paris, France
[21] Appl. No.: 719,313
[22] Filed: Apr. 3, 1985
[30] Foreign Application Priority Data

Apr. 6, 1984 [FR] France .................. 84 05490

[51] Int. Cl.⁴ ............................................. G01N 29/04
[52] U.S. Cl. ......................................... 73/622; 73/637; 73/638; 73/640
[58] Field of Search ................. 73/622, 623, 627, 638, 73/640, 621, 637, 634; 324/226

[56] References Cited

U.S. PATENT DOCUMENTS

| | | |
|---|---|---|
| 3,346,807 | 10/1967 | Wood et al. |
| 3,543,566 | 12/1970 | Sulmart ................................. 73/627 |
| 3,732,726 | 5/1973 | Ferber ................................. 324/226 |
| 3,926,040 | 12/1975 | Cowell ................................. 73/623 |
| 4,006,359 | 2/1977 | Sullins et al. ........................ 73/623 |
| 4,289,033 | 9/1981 | Prause et al. ........................ 73/622 |
| 4,506,549 | 3/1985 | Thane ................................... 73/622 |
| 4,523,468 | 6/1985 | Derkacs et al. ...................... 73/622 |

FOREIGN PATENT DOCUMENTS 0051089 12/1982 European Pat. Off. .
2239735 2/1974 Fed. Rep. of Germany .

*Primary Examiner*—Howard A. Birmiel
*Attorney, Agent, or Firm*—Browdy and Neimark

[57] ABSTRACT

For selective detection of microscopic defects in a workpiece to be checked presenting at least one macroscopic discontinuity of known nature, upon relative motion in respect to such workpiece according to a given check line, detecting the times when such check line meets a discontinuity, and searching for any possible defects in the workpiece intermittently for time intervals defined in reference to said times. This applies in particular to inspection of weld seams of welded tubes.

15 Claims, 4 Drawing Figures

METHOD AND INSTALLATION FOR SELECTIVE DETECTION OF DEFECTS IN A WORKPIECE

This invention relates to a method and an installation for selective (preferably automatic) detection of microscopic defects in a workpiece to be checked having at least one macroscopic discontinuity of known (especially metallurgic or geometric) nature.

The invention applies more particularly but not exclusively to nondestructive testing (in particular, by ultrasounds or eddy currents) of welded tubes.

As is known, welded tubes are sheets conformed to tubes of an appropriate cross-section (generally circular), then welded along longitudinal edges abutted to one another so as to present a substantially longitudinal (rectilinear or helical) weld seam. These sheets may be of very varied natures and qualities (in particular, steel, whether ferritic or austenitic, or special metals) and they result from various production processes (mainly continuous casting or ingots). However, depending on its preparation method and quality, a sheet contains more or less high quantity endogenic inclusions (for example, silicates, aluminates, titanium carbonitrides) which react to the nondestructive checking methods, in particular, ultrasonic beams, as they do to any internal defects. It results that a welded tube might be eliminated wrongly although it practically corresponds to the requirements imposed upon it and is entirely suitable to meet the requirements in operation. As a matter of fact, in order for the welded tubes to be accepted, even for top utilization requiring a high quality level (for example, the nuclear field), they must meet severe requirements mainly relating (or even only relating) to their welding seams. However, at the present time, unless it is done manually (with the possibility of being able to detect visually the weld seam, which is not always the case), it is not possible to distinguish defects as a function of their location relative to the weld seam and the thermally affected zones bordering it, and the welded tubes having a defective weld seam and the tubes welded irreproachably but where the basic sheet has intrinsic defects are all rejected indifferently. There results an artificially excessive rejection rate not representative of actual defects in the tubes considered, and the consequences of which may be significant.

The object of this invention is to eliminate this disadvantage by permitting selective deliberate detection of internal defects presented by weld seams (and the corresponding thermally affected zones) of welded tubes (preferably but not necessarily circular) and this, according to easily automated methods.

The invention applies to the very general field dealing with parts which may or may not be tubular presenting at least one macroscopic discontinuity of known nature (welding seam, groove...) predetermined zones of which, defined by their position relative to such discontinuity, are to be tested separately. This invention can actually be applied a contrario in the field of welded tubes for checking the basic sheet, apart from the weld seam and the associated thermally affected zones.

To this end, there is proposed according to the invention, a method of selective detection of microscopic defects in a workpiece to be checked having at least one macroscopic discontinuity of known nature through relative movement in respect to such workpiece along a given check line, characterized by noting the times when such a check line meets a discontinuity, and searching for any possible defects of the workpiece intermittently during given time intervals as defined by referring to said times.

The invention applies more particularly to the checking of tubes, in particular, welded tubes, and as the selected line for realizing such checking is conventionally a helical line with very close spires so as to cover all of the tube bulk, the invention provides for the checking to be selectively carried out on an angular sector mainly encompassing the weld seam and the thermally affected zones bordering it. This invention also specifies non exclusively that the macroscopic discontinuity and the microscopic defects should be detected by analyzing return signals received in response to ultrasonic pulses. As regards the defects, two cases are possible, i.e. either the received return signals are intermittently analyzed in response to a continuous series of pulses, or such pulses are transmitted in discontinuous trains. When it is performed both for the discontinuity and defects by transmission of ultrasonic pulses, such pulses are advantageously synchronized with such a frequency which is preferably servo-controlled to the speed the check line is travelled through; more precisely, in case of a helical check line, such frequency is advantageously related linearly to the angular component of such speed.

For carrying out this method, the invention proposes an installation for selective detection of microscopic defects in a workpiece to be checked presenting at least one macroscopic discontinuity of known nature comprising a defect sensor mounted with relative motion in respect to such workpiece according to a given check line, characterized in that the defect sensor is associated with an intermittent control unit and the defect sensor is associated with a detector responsive to such discontinuity, for transmitting when the discontinuity is detected, a triggering signal to the intermittent control unit of said defect sensor, such unit being adapted to trigger the sensor after a time delay for a predetermined time interval responsive to such signal. This installation is advantageously automatic.

The defect sensor and the discontinuity detector are advantageously ultrasonic transducers (for example, of the same type) preferably synchronized by a timing pulse generator servo-controlled to the relative speed between the sensor (and the detector) and the workpiece to be checked. In case of welded tubes, the detector will be selected so as to present such characteristics as to be able to detect a weld seam; preferably, it is an ultrasonic transducer oriented in a direction close to the centerline, whereas the defect sensor will be preferably an ultrasonic transducer oriented in a transverse plane. In case of tubes driven in a translational movement, through a rotor (carrying the sensor and the detector) driven into rotation, the pulses of this sensor and detector are advantageously synchronized as a function of the rotational speed of such rotor, for example by means of a toothed wheel and a proximity detector or an optic encoder. The control circuit of the defect sensor intermittently controls either the ultrasonic pulses or the processing of the resulting return signals. In the latter case, the control circuit advantageously causes distribution of the return signals into different processing channels corresponding to the various zones of inspection as defined on the workpiece to be checked. The number of sensors or detectors is not limited to one.

In a preferred mode of embodiment, the installation according to the invention is a conventional checking installation designed for providing as desired complete inspection of the workpiece bulk as is done nowadays, or selective checking according to the method of the invention.

Other objects, characteristics and advantages of this invention will appear from the following description given by way of a non limitative example in reference to the attached drawings in which.

Figure 1:
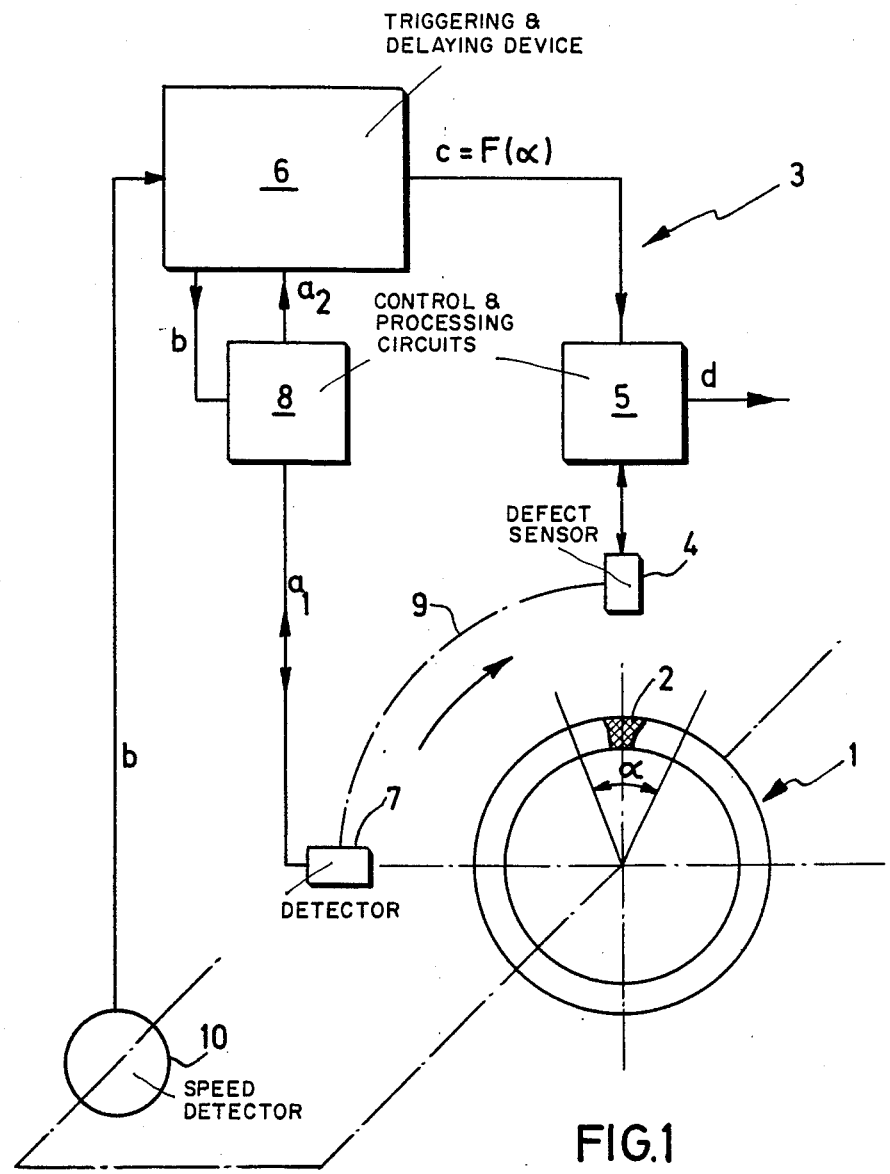
FIG. 1 is a schematic simplified view of an installation according to the invention.

FIG. 1 shows by way of example and schematically a simplified form of embodiment of an installation according to the invention adapted to the checking of welded tubes 1 presenting a weld seam 2, for example, rectilinear and longitudinal. The selective detection installation 3 associated therewith is automatic and mainly comprises a defect sensor 4 associated with a control and processing circuit 5 itself disposed opposite the tube 1 and placed under the control of a triggering and delaying device 6. A detector 7 responsive to the discontinuity constituted by the weld seam 2 is moreover disposed opposite the tube 1; it is associated with a control and processing circuit 8 connected to the above mentioned triggering and delaying device 6. The defect sensor 4 and the detector 7 are in practice mounted to the same movable carrier 9 shown schematically by dot-dashed lines.

In the exemplifying form of embodiment considered, the sensor 4 and the detector 7 are both ultrasonic transducers. In view of the tasks assigned thereto the detector is advantageously oriented in an axial plane, whereas the sensor is preferably oriented in a transverse plane. These transducers generally make an angle of about 20° relative to the surface of the tube. In view of the arrangement of the sensor 4 it is adapted to especially detect defects disposed axially (longitudinal direction): practically it is this type of defects which are more appropriately to be detected. In a modified form of embodiment, a complementary sensor is associated therewith to detect defects disposed transversely (transverse direction). According to another modified form of embodiment, not shown, the detector 7 and the sensor 4 are punctual eddy current probes.

Mechanical problems and any possible ultrasonic interference problems cause the detector 7 and the sensor 4 to be preferably disposed such that ultrasonic beams transmitted therefrom intercept the tube in differing transverse planes.

The triggering and delaying device 6 controls for sensor 4 and detector 7 ultrasonic pulses synchronized according to a frequency which advantageously varies with the relative speed between said transducers 4 and 7 and the tube 1, preferably with the angular component of the speed. Such speed is detected by a speed detector 10 adapted to generate synchronizing pulses denoted b, the frequency of which varies according to a preferably linear law with the relative speed between transducers and tubes. These pulses b are transmitted to the device 6; they are the base for the triggering of the operation of sensor 4. To obtain reliable checking it is appropriate for the pulse frequency b to be of the same order of magnitude as the recurrent frequency of the ultrasonic device considered (i.e. as the number of excitations received in one second by ultrasonic trannsducers 4 and 7). In a conventional manner such frequency is about 10 kHz. If need be, pulses b are applied to a frequency multiplier to obtain an appropriate final frequency.

The speed detector 10 is the proximity detector disposed opposite a toothed wheel rotatably locked to the transducers in the case of FIG. 1 in which the tube is driven into a translational movement along its centerline while the transducers are driven into rotation. By way of example, the transducers are driven at a speed of 6000 revolutions per minute and 100 crenels are formed in the toothed wheel so that the desired frequency of 10 kHZ is obtained.

Figure 2:
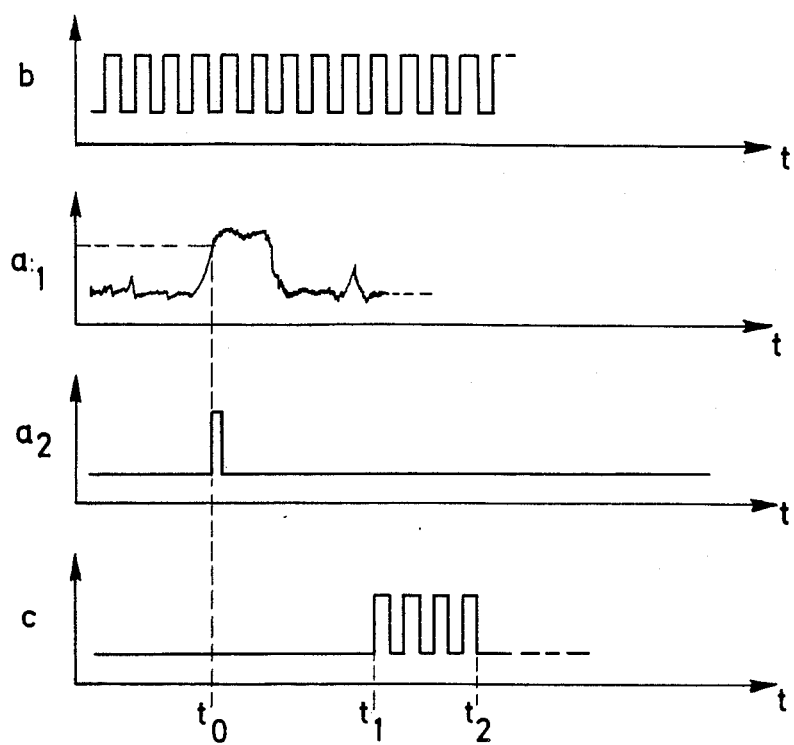
FIG. 2 is a diagrammatic view showing development in the course of time of the main signals appearing therein.

In operation, the installation of FIG. 1 is travelled through by signals having a development in the course of time as illustrated in FIG. 2. The pulses b are taken into account by the device 6 and the circuit 8 for driving the detector 7. This detector 7 receives a return signal a1 the background noise level of which increases on passing the metallurgic discontinuity constituted by the weld seam 2 up to exceeding a reference level at a time $t_0$. The circuit 8 then transmits a triggering signal a2 to the device 6. After reception of such signal the device 6 triggers the circuit 5 after a predetermined number of pulses b corresponding to a given time interval ($t_1-t_0$) for a second predetermined number of pulses b corresponding to a given time interval ($t_2-t_1$) (signal c); the sensor 4 then inspects the tube on an angular sector of the amplitude $\alpha$ defined so as to only cover the weld seam 2 and the thermally affected zones bordering it. Such amplitude is in practice defined by calibration with a tube presenting standard defects. By way of example, with a tube of a diameter of 50 mm, the amplitude $\alpha$ is about 30°. There is thus obtained on the output d from circuit 5 a measurement signal that only takes into account any possible defects as mentioned above in or close to the weld seam. In a modified form of embodiment, the sensor 4 is permanently excited and the circuit 5 directs the measurement signal to one or the other of two processing circuits corresponding to the angular sector $\alpha$ or its complement.

The precision of the definition of the angular sector obviously depends on the number of pulses b that are transmitted by one revolution of the toothed wheel.

In a modified form of embodiment, when the rotation is not applied to transducers 4 and 7 but rather to the tube, the pulses b are generated by an optic encoder.

Figure 3:
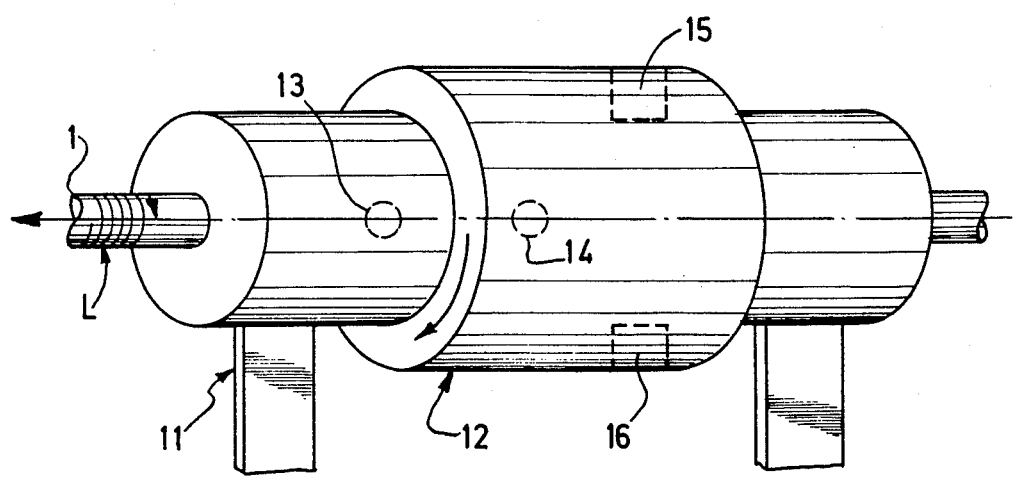
FIG. 3 is a simplified perspective view of an installation according to the invention according to another form of embodiment.
Figure 4:
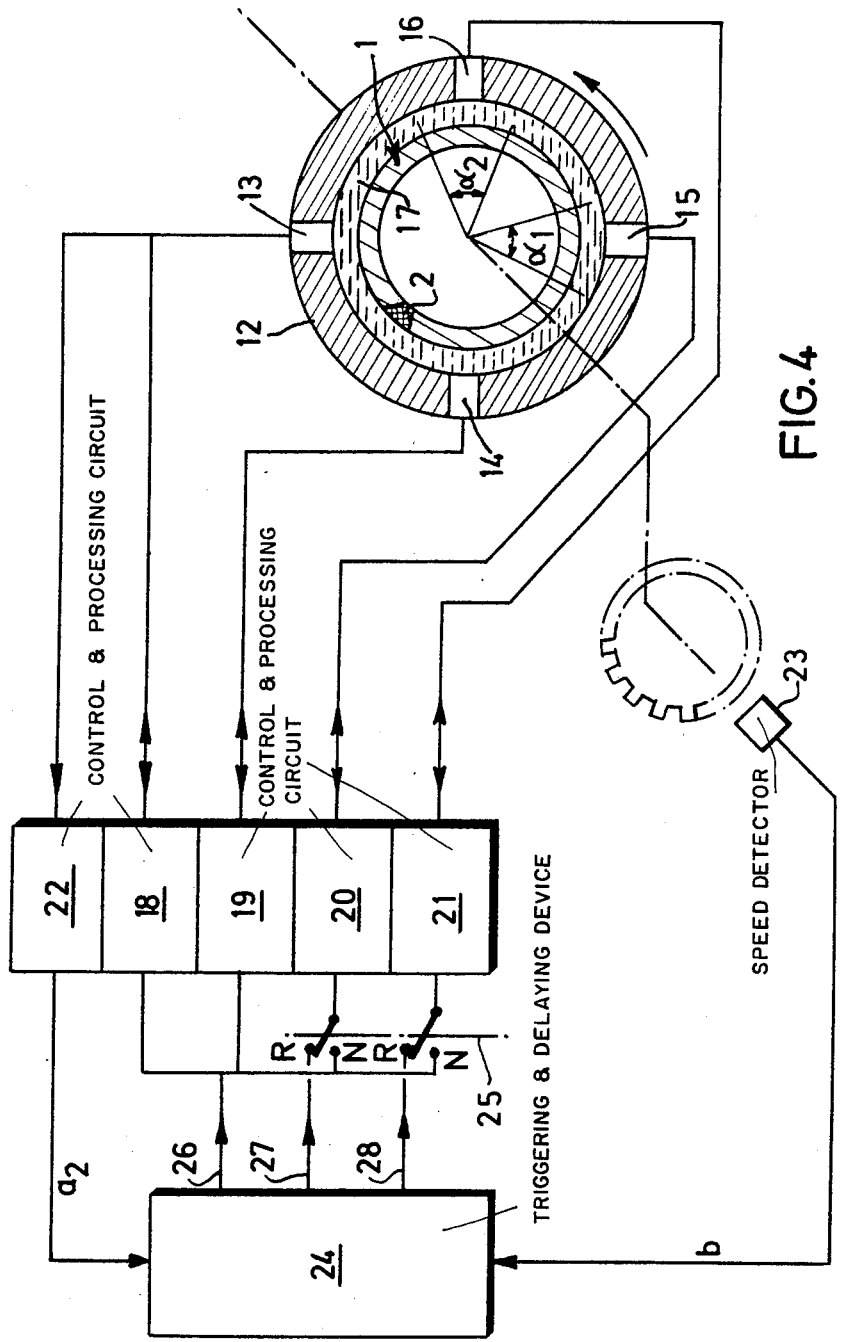
FIG. 4 is a simplified schematic view thereof.

FIGS. 3 and 4 illustrate an installation adapted to provide as desired for total or selective checking of a tube 1 to be tested according to a helical (dummy) line L.

FIG. 3 shows a tube 1 axially slidable relative to a stator 11 to which a rotor 12 is rotatably mounted, such rotor carrying two pairs of ultrasonic tranducers 13 and 14, and 15 and 16 disposed in different planes and adapted to detect defects oriented in the transverse direction and the longitudinal direction under several respective angles. A water film 17 is obviously maintained permanently between such transducers and the tube 1. This configuration is conventional and is currently used for conventional testing of tubes.

Each of the transducers 13 through 15 is associated with a control and processing circuit 18, 19, 20 and 21, respectively. The transducer 13 is moreover associated with a second control and processing circuit 22.

As appears from FIG. 4 a speed detector 23 and a triggering and delaying device 24 similar to elements 10 and 6 in FIG. 1 are associated with the circuits 18 through 22 according to two possible modes of connection selected by means of a switch 25 connected to the inputs to the circuits 20 and 21 associated with the sensors 15 and 16.

In the normal mode (N) the device 24, depending on the pulses b from the speed detector 23, provides for synchronized driving of circuits 18 through 21 through its output 26; the four transducers 13 through 16 all detect the tube 1 defects and transmit corresponding measurement signals according to several channels, not shown. The circuit 24 in this case is only used for synchronization.

In a renewal mode (R) and the tube 1 being submitted to a new testing cycle, the transducer 13 is also used as a discontinuity detector as is detector 7 of FIG. 1, with the associated circuit 22 then processing the return signals received by the transducer 13 so as to transmit to device 24 a triggering signal when the weld seam is detected. Such device 24 then causes by its outputs 27 and 28 intermittent triggerings of transducers 15 and 16 for equal but offset time intervals as defined by predetermined numbers of pulses transmitted from the speed detector 23 so as to make them scan successively identical angular sectors $\alpha_1$ and $\alpha_2$ on the tube.

It is to be noted that the diagram of FIG. 4 was simplified to make it more easily readable; thus, none of the output channels from circuits 18 through 28 was shown. Moreover, the transducers have been grouped by functions, whereas they are diametrically opposite by pairs in FIG. 3.

In fact, the control and processing circuits of transducers (5, 8 and 18 through 21) are conventional circuits readily adaptive to the invention needs and do not require any specific instruction to enable the man of the art to use them. Similarly, synchronization, triggering and delaying devices may readily be realized by taking into account the indications given above relative to their function and object.

It will be understood that the foregoing description was proposed by way of indicative example and that many variations thereof can be proposed by the man of the art without however departing from the scope of the invention.

The invention is especially adapted to checking circular welded tubes with a thin wall (for example, of a diameter of 19 mm and a thickness of 1.8 mm), but it can be generalized to other types of workpieces; if need be, it is appropriate to provide correction of the output signals from the sensors and the detectors as a function of any possible variations in their orientation and distance relative to the outer surface of the workpiece to be tested. It is to be noted that if a weld seam is inspected the detector must be responsive to the difference in the associated structure; the more attenuated such structure variation, induced by the welding operation, due to any subsequent thermomechanical treatment, the more difficult will be the carrying out of the invention.

It is also to be noted that when the sensor(s) and the detector(s) are driven into rotation about a tube, their electric connection to the associated circuits comprises rotary contacts which may be in particular and in a known manner connections by rotary capacitors or rotary self-inductors, or else brushes slidable on tracks.

In a simplified form of embodiment of the invention the time base constituted by the speed detectors 10 or 23 may be in a modified form of embodiment independent of the relative motion between sensors (and detectors) and the workpiece and suppy synchronization pulses at a required constant frequency.

It will be noted that the defect sensor is disposed and oriented so as to detect defects but not the macroscopic discontinuity whereas the detector is disposed and oriented so as to detect the macroscopic discontinuity but not any possible defects.

I claim:

1. A method for selectively detecting microscopic defects in a workpiece to be checked including a macroscopic elongated discontinuity of known nature comprising the steps of:
    providing on a support means defect sensor means facing said workpiece and adapted to detect such microscopic defects in said workpiece and detector means facing said workpiece and adapted to detect said macroscopic discontinuity;
    mounting said support means with continuous relative motion in respect to said workpiece along a predetermined check line crossing said macroscopic discontinuity;
    detecting at least one time at which said macroscopic discontinuity is detected by said detector means;
    defining in a predetermined manner at least one time interval with reference to said at least one detected time and scanning said workpiece during said at least one time interval only, said at least one time interval being determined so that there is scanned on said workpiece a given area defined with respect to said elongated macroscopic discontinuity.

2. A method for selectively detecting microscopic defects in a welded metallic tube to be checked comprising a weld seam extending along said tube and bordered by two thermally affected zones comprising the steps of:
    providing on support means defect sensor means facing said metallic tube and adapted to detect such microscopic defects in said workpiece and detector means facing said metallic tube and adapted to detect said thermally affected zones:
    mounting said support means with relative motion in respect to said metallic tube along a predetermined helical line crossing said weld seam;
    detecting times at which said weld seam is detected by said detector means;
    defining in a predetermined manner time intervals with reference to said detected timers and scanning said metallic tube during said time intervals only, said time intervals being defined so that there is scanned on said metallic tube an area extending along said weld seam on either part thereof.

3. A method according to claim 2, wherein said detector means is adapted to transmit ultrasonic waves towards the metallic tube and receive reflected ultrasonic energy, and wherein said times at which the weld seam is detected by said detector means are defined by said reflected ultrasonic energy growing higher than a threshold value.

4. A method according to claim 3, wherein said defect sensor means is adapted to transmit ultrasonic waves towards the metallic tube and receive reflected ultrasonic energy, and said metallic tube is scanned by transmitting such ultrasonic waves during said time intervals only.

5. A method according to claim 3, wherein said defect sensor means is adapted to transmit ultrasonic waves towards and receive reflected ultrasonic energy, and said metallic tube is scanned by continuously transmitting ultrasonic waves towards the metallic tube but taking into account received reflected ultrasonic energy during said time intervals only.

6. A method according to claim 2, wherein said defect sensor means and said detector means are respectively controlled so as to transmit towards said metallic tube synchronized ultrasonic waves.

7. A method according to claim 6, wherein said synchronized ultrasonic waves are transmitted at a frequency depending on instantaneous relative angular speed of said support means with respect to said metallic tube.

8. A system for selectively detecting microscopic defects in a workpiece to be checked including a macroscopic elongated discontinuity of known nature comprising:
   support means in relative motion in respect to the workpiece along a predetermined check line covering said macroscopic discontinuity;
   defect sensor means adapted to detect such microscopic defects in the workpiece, and detector means adapted to detect said macroscopic discontinuity, said defect sensor means and said detector means being carried by said support means so as to face the workpiece;
   an intermittent control unit for said defect sensor means connected so as to receive an output signal from said detector means, said detector means being adapted, when said macroscopic discontinuity is detected, to transmit a triggering signal to said intermittent control unit, said unit being adapted, when receiving such triggering signal, to trigger said defect sensor means during a given time period after a predetermined time delay.

9. A system according to claim 8, wherein said defect sensor means and said detector means are ultrasonic transducers which are controlled in synchronism by triggering and delay device.

10. A system according to claim 9, wherein said defect sensor means and said detector means are controlled depending on synchronization pulses transmitted from speed detector means responsive to relative speed of said support means with respect to the workpiece.

11. A system according to claim 10, wherein the workpiece being a metallic tube provided with an elongated weld seam and said support means being mounted with relative motion in respect to said metallic tube along a predetermined helical line crossing said weld seam, said speed detector means are responsive to relative speed of said support means with respect to the workpiece.

12. A system for selectively detecting microscopic defects in a metallic tube to be checked provided with an elongated weld seam comprising:
   support means in relative motion with respect to said metallic tube along a predetermined helical check line crossing said weld seam;
   defect sensor means comprising at least an ultrasonic transducer carried by said support means so as to face said metallic tube while being oriented in a plane transverse to said metallic tube;
   detector means for detecting said weld seam comprising at least an ultrasonic transducer carried by said support means so as to face said metallic tube while being oriented in a plane containing the axis of said metallic tube;
   a intermittent control unit for said defect sensor means and said detector means connected so as to receive an output signal from said detector means, said detector means being adapted, when said weld seam is detected, to transmit a triggering signal to said intermittent control unit, said unit being adapted, when receiving such triggering signal, to trigger said defect sensor means during a given time period after a predetermined time delay, said detector means and said defect sensor means being controlled in synchronism by a triggering and delay device.

13. A system according to claim 12, wherein said defect sensor means is activated by said intermittent control unit during such given time periods only.

14. A system according to claim 12, wherein ultrasonic energy reflected by said metallic tube and received by said defect sensor means is taken into account by either a first processing channel during such time periods or a second processing channel.

15. An ultrasonic inspection system for checking a metallic tube provided wih an elongated weld seam comprising:
   (a) support means in relative motion with respect to said metallic tube along a predetermined helical check line crossing said weld seam;
   (b) a first pair of ultrasonic transducers oriented in a same transverse plane with the metallic tube and a second pair of ultrasonic transducers oriented in planes containing the axis of said tube, said first and second pairs of ultrasonic transducers being carried by said support means;
   (c) a control unit comprising a common terminal and a pair of specific terminals, connected to said first pair of ultrasonic transducers through switch means adapted to connect said first pair to either said common terminal or said pair of specific terminals, and connected to said second pair of ultrasonic transducers, one transducer of said second pair being further connected to said control unit through a selective control unit, said control unit being adapted, when said switch means is in a first position, to activate continuously said first and second pairs of ultrasonic transducers for total inspection of said tube and, when said switch means is in a second position, to selectively and successively trigger said ultrasonic transducers in said first pair so that they scan one and the same area on the metallic tube, during time periods defined in reference to times at which said weld seam is detected by said ultrasonic transducer of said second pair which is connected to said selective control unit, for selective inspection of said metallic tube.

* * * * *